(12) United States Patent
Jensen

(10) Patent No.: US 12,740,828 B2
(45) Date of Patent: Sep. 22, 2026

(54) SYSTEMS AND METHODS OF CUTTING HARD AND SOFT BIOLOGICAL TISSUE UTILIZING RADIANT ENERGY AND DYES

(71) Applicant: CAO Group, Inc., West Jordan, UT (US)

(72) Inventor: Steven D Jensen, South Jordan, UT (US)

(73) Assignee: CAO Group, Inc., West Jordan, UT (US)

( * ) Notice: Subject to any disclaimer, the term of this patent is extended or adjusted under 35 U.S.C. 154(b) by 245 days.

(21) Appl. No.: 18/270,676

(22) PCT Filed: Dec. 31, 2021

(86) PCT No.: PCT/US2021/065838
§ 371 (c)(1),
(2) Date: Jun. 30, 2023

(87) PCT Pub. No.: WO2022/147361
PCT Pub. Date: Jul. 7, 2022

(65) Prior Publication Data

US 2024/0065761 A1 Feb. 29, 2024

Related U.S. Application Data

(60) Provisional application No. 63/133,057, filed on Dec. 31, 2020.

(51) Int. Cl.
*A61B 18/20* (2006.01)
*A61B 18/00* (2006.01)

(52) U.S. Cl.
CPC .... *A61B 18/20* (2013.01); *A61B 2018/00601* (2013.01); *A61B 2018/202* (2013.01)

(58) Field of Classification Search
CPC .................... A61B 18/20; A61B 18/22; A61B 2018/00577; A61B 2018/00601; A61B 2018/202; A61B 2018/2266; A61B 2018/2272; A61B 2018/263; A61C 1/0046
See application file for complete search history.

(56) References Cited

U.S. PATENT DOCUMENTS

2008/0188840 A1* 8/2008 Johnson ............... A61B 18/203 606/9
2016/0041100 A1* 2/2016 Mizoguchi ......... G01N 21/6486 549/33

* cited by examiner

*Primary Examiner* — Khadijeh A Vahdat
(74) *Attorney, Agent, or Firm* — Dobbin IP Law PC; Geoffrey E. Dobbin

(57) ABSTRACT

A laser system for hard and soft biological tissues utilizes a laser (206), dye spray applicator (205), and a rinse spray applicator (212) in concert within a single handpiece (200) to create a computer programmable system that delivers a precise means of controlled ablation. The handpiece (200) is first used to apply dye (209) to a targeted treatment surface (210). Then it is used to apply a laser beam to the dyed treatment surface. This is followed by applying a rinse agent (215) through the same handpiece (200) to remove debris and combustion by-products. The steps are then repeated until the operation is complete.

4 Claims, 5 Drawing Sheets

SYSTEMS AND METHODS OF CUTTING HARD AND SOFT BIOLOGICAL TISSUE UTILIZING RADIANT ENERGY AND DYES

CROSS-REFERENCES TO RELATED APPLICATIONS

This Application claims the priority to and the benefit of prior filed U.S. Application 63/133,057, filed Dec. 31, 2020, and incorporates the same by reference herein in its entirety.

FIELD OF THE INVENTION

The present invention relates to the field of surgical instruments and more particularly relates to a surgical cutting tool which both applies a dye and a laser attuned to the dye to a surface to be cut.

BACKGROUND OF THE INVENTION

There is a surgical need in the medical and dental industry to have the ability to efficiently and precisely cut both hard and soft physiological tissues. There are many tools in the art which are currently available on the market today, such as a scalpel, drill, saw, excavators, and many other tools, whereby these various surgical methods are accomplished. One of the newest inventions for this purpose is the laser; whereby an appropriately powered and focused laser is utilized to cut soft and hard tissue by various methods. Laser has many benefits for medical usage. However, cutting soft or hard tissues by laser depends upon the absorption efficiency of laser energy by tissues and different tissues have different absorption rates for different laser wavelengths. It is impossible for one wavelength to cut all types of tissues without generating excessive heat, which is detrimental to surrounding good tissues.

The present invention is a novel advancement in the art that utilizes a high-powered laser coupled with a matching wavelength absorptive dye, stain, or pigment to adjust absorption rate of tissue to the laser and make cutting efficiently at lower energy without generating excessive heat.

The present invention represents a departure from the prior art in that the laser cutting system of the present invention allows for direct application of a dye, laser, and rinse solution to tissues desired to be cut with the same tool.

SUMMARY OF THE INVENTION

In view of the foregoing disadvantages inherent in the known types of cutting systems an improved laser cutting system may provide a system that meets the following objectives: that it be able to cut both hard and soft tissue, that it be simple to operate and manufacture, and that it would generate less heat than traditional systems. As such, a new and improved laser system may comprise a mechanism to deliver a laser beam to a cutting surface, a mechanism to apply a dye to the cutting surface, and a mechanism to deliver a rinsing solution to the cutting surface to clean off the debris caused by cutting the targeted tissues. The dye should have a high absorption efficiency in relation to the emitted laser energy. The method of cutting a targeted tissue structure is simple. First, a dye solution is applied to the targeted surface through the dye application mechanism. Then a laser beam having a proper power output and pulse rate is applied to the dyed surface, resulting in ablation of the surface. After this, a solution may be applied to clean off the dye and debris from ablation. This sequence is repeated until the desired cutting is achieved and all three steps are completed with the same tool and handpiece. The invented method will cut all the tissues efficiently at lower laser energy with fewer heat issues.

The more notable features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in several ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions as far as they do not depart from the spirit and scope of the present invention.

DETAILED DESCRIPTION OF THE PREFERRED EMBODIMENT

With reference now to the drawings, a preferred embodiment of the laser cutting system is herein described. It should be noted that the articles "a," "an," and "the," as used in this specification, include plural referents unless the content clearly dictates otherwise.

The present invention utilizes a laser, dye spray applicator, and a rinse spray applicator together in concert to create a computer programmable system that delivers a precise means of controlled ablation. The laser module, spray applicator and rinse applicator are integrated into a single unit that is activated by the main interface, a foot switch or hand piece. The laser portion comprising a laser module that is coupled to a fiber optic cable or tip, wherein the coherent radiant energy is delivered directly to the treatment site. The dye spray activator comprises a liquid dye storage container and a pump, which is connected by means of tubing to a nozzle that is designed to spray a pattern of stain onto the treatment site that best matches the radiant energy footprint from the fiber optic. The rinse applicator comprises a rinsing liquid storage container and a pump that is connected by means of tubing to a nozzle that is designed to rinse the treatment site. The nozzles of the stain and rinse applicators can be attached directly to the end of the fiber optic cable or hand piece such that by simply aiming the laser all 3 steps of dye application, laser initiation, and rinsing can be done continuously in succession by triggering the foot switch or other triggering device, thereby allowing the operator to continuously ablate as desired.

Figure 1:
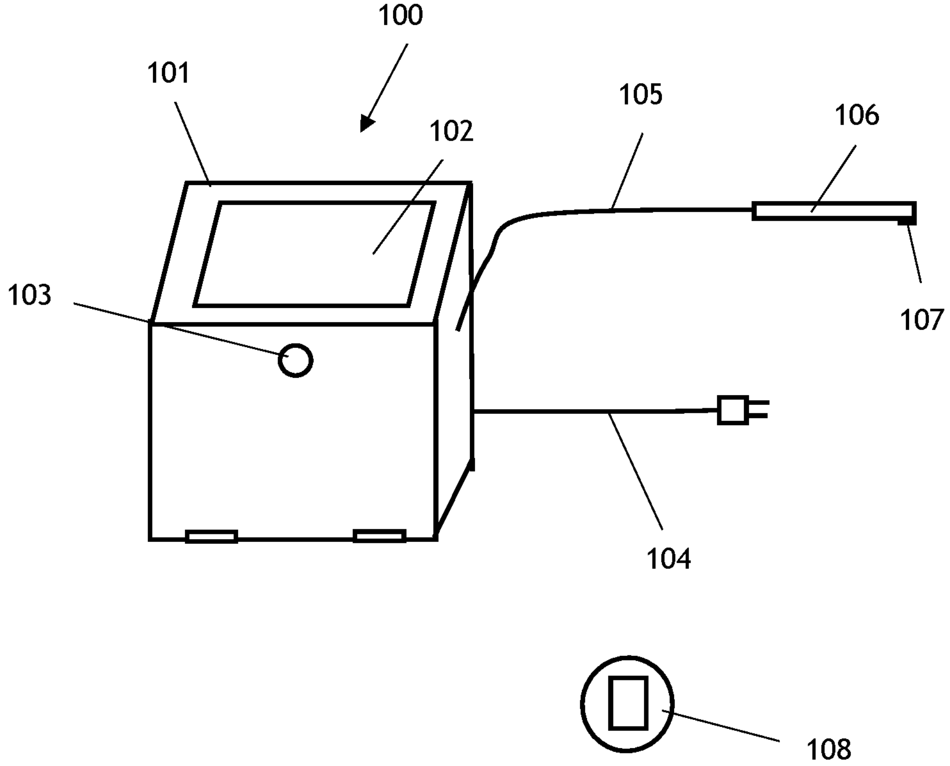
FIG. 1 is a schematic drawing of a laser cutting system utilizing an embodiment of the invention.

The integrated system is controlled by means of a programmable computer module that controls the laser power output and the duration of the pulse; it also controls the pump for both the stain applicator and the rinse applicator such that a precise amount of the liquid components and/or the duration of flow can be precisely controlled and delivered at the specified time. As seen in FIG. 1, a laser system to cut both hard and soft tissue (100) has a casing (101) with a display (102) for laser system information and control. An emergency stop button (103) may be provided to intervene laser at any given time. A power supply (104) to provide power to the system is depicted, however the system can also be rechargeable battery operated. The system may be controlled by any means, however a wireless footswitch (108) is commonly utilized to control emission of the laser system (100). Controls may also be positioned on the handpiece itself. A multifunction cable (105), containing fiber waveguide for a laser beam, electrical wires, and tubing to deliver desired liquids, is also connected to the system, and runs through handpiece (106) which is held by the operator. Handpiece (106) supports multifunction cable (105) and presents exits for the laser beam and liquids (107). A laser beam is generated from a laser module generated inside the laser system casing. The liquids can be transported through cable (105) from liquid reservoirs inside the system or may be stored in micro cartridges placed in the handpiece (106).

Figure 2:
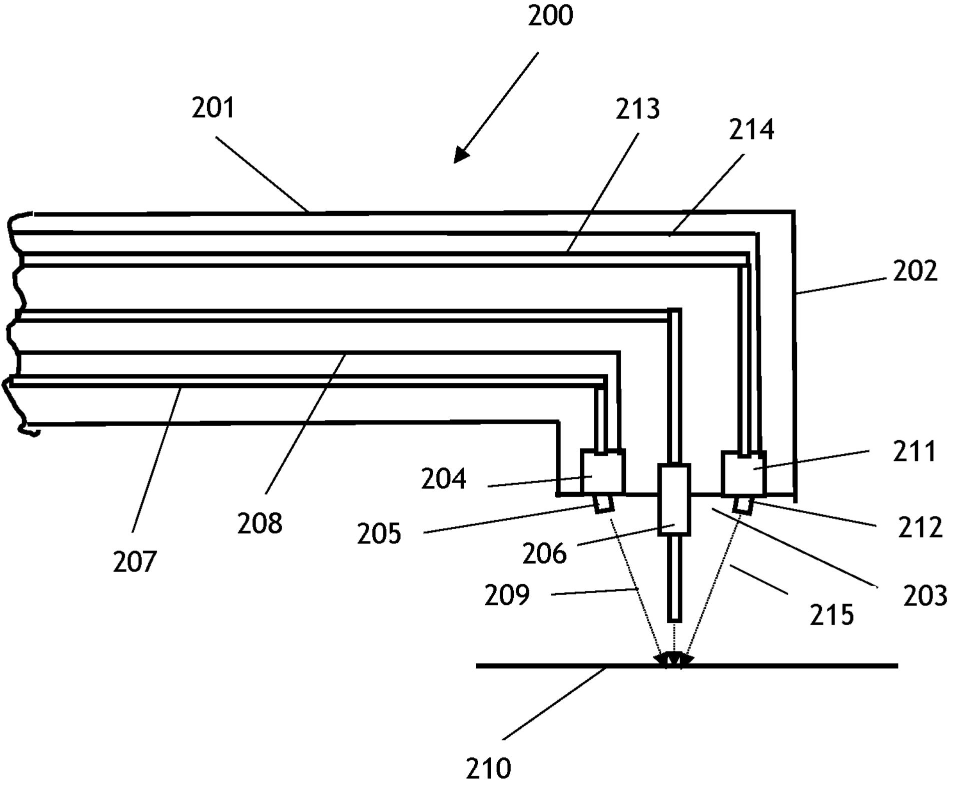
FIG. 2 is a close-up schematic of the head of the laser cutting system in FIG. 1.

The handpiece has a head (200), which may be one of many different embodiments. One embodiment is shown in FIG. 2, featuring a casing (201) with distal end (202) and an exit (203) for laser (206) and liquids. At exit (203), there is a microvalve (204) connected to tubing (207) to deliver dye to microvalve (204), with a nozzle (205) for delivery. In this embodiment, the dye is stored in a reservoir in the laser system. There is a wire harness (208) to connect the microvalve (204) and control the microvalve from the system. The emission of the dye is controlled by microvalve (204) through nozzle (205) to form a dye jet (209) to apply the dye to the treatment surface (210). There is also a microvalve (211) with a nozzle (212) of a rinse agent. As with the dye, tubing (213) delivers the rinse solution to microvalve (211) from a reservoir in the laser system. There is a wire harness (214) connected to the microvalve (211) for control. The emission of the rinse solution is emitted through nozzle (212) as a rinse jet (215) to the treatment surface (210). The laser (206), dye jet (209), and rinse jet (215) may be focused on a single spot area of the treatment site, as is shown in FIG. 2.

In use, the laser beam will have certain wavelength and power. The wavelength can be one of followings: any wavelength can be generated by semiconductor lasers, any wavelength that can be generated by diode pumped lasers, any wavelength that can be generated by solid state lasers, any wavelength that can be generated by gas lasers. The power output of laser beam can be ranged for 1 W to 100 W. The laser being selected to produce a narrow wavelength of coherent light such that it can be matched to a dye that will absorb the energy at an efficiency of greater than 50%, and more especially at an efficiency above 90%. The radiant energy is produced by various means as described, but the preferred radiant energy source is a diode laser. The cutting implements according to present invention may utilize laser density as low as 1 watt and up to about 100 watts output. The laser output can be in continuous or pulsed format depending on the requirements of laser power and dye to be used.

The first liquid in the system is a dye, stain, or pigment that efficiently absorbs radiant energy and transforms it back into heat. Collectively, these will be referred to as "dyes." Examples of dyes usable according to the teachings of the present invention include, but are not limited to, are: carbon black, FD&C Blue #2, nigrosin, FD&C black shade, FD&C blue #1, methylene blue, FD&C blue #2, malachite green, D&C green #8, D&C green #6, D&C green #5, ethyl violet, methyl violet, FD&C green #3, FD&C red #3, FD&C red #40, D&C yellow #8, D&C yellow #10, D&C yellow #11, FD&C yellow #5, FD&C yellow #6, neutral red, safranine O, FD&C carmine, rhodamine G, napthol blue black, D&C orange #4, thymol blue, auramine O, D&C red #22, D&C red #6, xylenol blue, chrysoidine Y, D&C red #4, sudan black B, D&C violet #2, D&C red #33, cresol red, fluorescein, fluorescein isothiocyanate, bromophenol red, D&C red #28, D&C red #17, amaranth, methyl salicylate, eosin Y, lucifer yellow, thymol, dibutyl phthalate, indocyanine green, and the like. The preferred dye is one that is deemed biologically compatible or non-toxic and may include any of the above dyes as an ingredient in a final solution. Other dyes, currently existing or discovered or manufactured in the future, may be readily utilized in this method. Therefore, the above listing should not be considered definitive, but illustrative of dyes to be utilized in the disclosed method and in no way be considered limiting.

The second liquid in the system is a liquid that can wash off the dyes after laser interaction from tissue. An embodiment of the present invention utilizes a washing or rinsing step that is designed to remove residual decomposition and contamination components from the treatment site after the dye and laser steps have initiated and fired. These actions will produce residual contaminants, including by-products of combustion and thermally decomposed tissue, which need to be removed from the treatment site. If these contaminants are not removed, they will significantly decrease the efficiency of the next laser/dye cycle. A rinse or wash step is designed to remove these contaminants before the next cycle begins. Examples of rinsing solvents and solutions include but are not limited to water; solutions of salts in water, such as sodium chloride; alcohol solutions; poly-ol solutions; surfactants; and any other useful rinsing agent.

Initially, in one embodiment of the method of the invention, the dye in liquid form is systematically micro-sprayed onto the treatment site as a pulse. Immediately thereafter, the laser is triggered, and a pulse of radiant energy is directed to the treatment site where it is absorbed by the liquid dye, creating extreme localized heating. This heating causes rapid expansion, and a micro explosion soon follows which cuts both the hard and soft tissue. Finally, a cleansing spray is pulsed over the treatment site to wash and clean the treatment site before the entire process is repeated in rapid succession thus creating a system to cut biological tissue efficiently and precisely. The dyes are specifically selected to efficiently match the output of the radiant energy source and thus maximize energy absorption. This efficient absorption translates the energy into faster heat conversion and better cutting efficiency.

An example of a treatment cycle with the present invention is as follows:

1. Spray the laser treatment site with a radiant energy absorptive dye (209) that is matched to the output of the laser.
2. Initiate the laser (206), wherein the stained area becomes thermally heated to such an extent that ablation occurs at the surface (210).
3. Rinse and cleanse the area from residual contaminants by means of a pressurized jet of rinsing liquid (215) that directly blasts the treatment site.
4. The cycles of dye, laser, rinse will repeat until desired cutting results are achieved.

Figure 3:
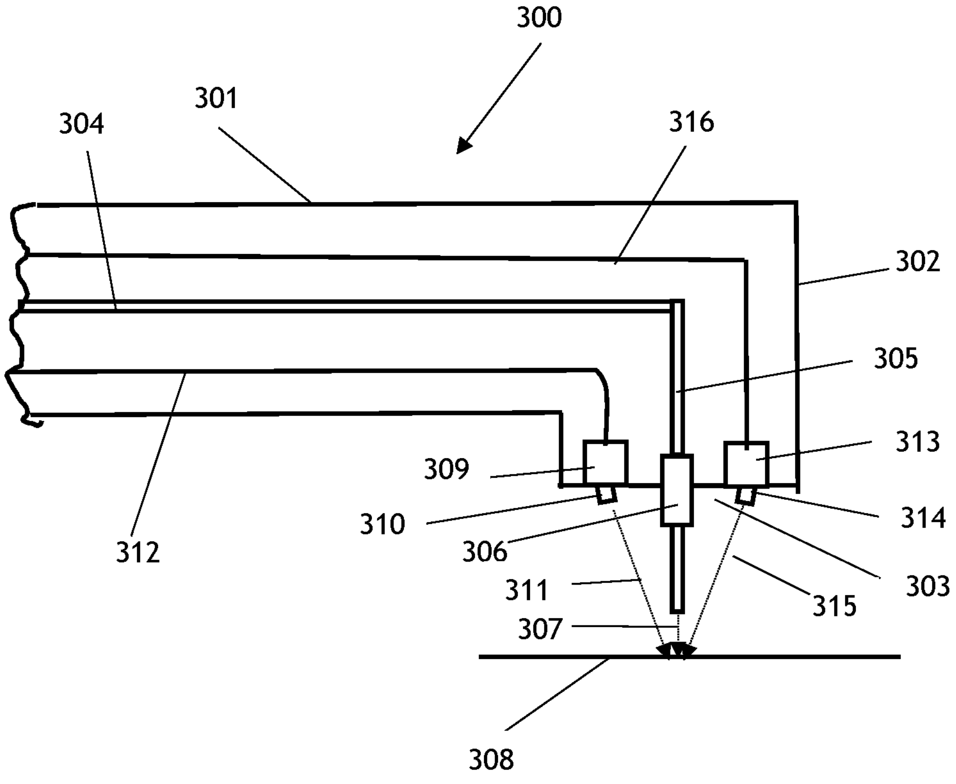
FIG. 3 is a schematic depicting an alternate head design, with reservoirs for liquids stored therein.

An alternate handpiece construction is shown in FIG. 3, where (300) is a handpiece for the laser system, with (301) being a handpiece casing with a proximal end and distal end (302) with an exit (303) for laser (307), dye (209), and rinse solution (315). Inside the handpiece (301), there is a fiber (304) from laser system to deliver a laser beam. This fiber cable (304) is turned 90° (305) and ends before the handpiece exit. The laser beam can be optically shaped into a replaceable fiber tip (306) which delivers the laser beam (307) to the treatment surface (308). The handpiece contains two liquid cartridges (309), (313) located proximate laser tip (306). Cartridge (309) contains a dye solution and has a nozzle (310) positioned to spray a dye jet (311) on the treatment surface (308). There is a wire (312) connected the cartridge (309) to the laser system to control emission of the dye jet (311). The amount of solution injected from cartridge and speed are controlled electronically. Rinse cartridge (313) contains rinse solution and like the dye cartridge has a nozzle (314) positioned to spray the rinse solution (315) on the treatment surface (308). There is a wire (316) connecting the cartridge (313) to the laser system to control emission of rinse solution to surface. The amount of solution injected from cartridge and speed are controlled electronically. Both cartridges (309), (313) are replaceable when the liquids in the cartridge are consumed.

Figure 4:
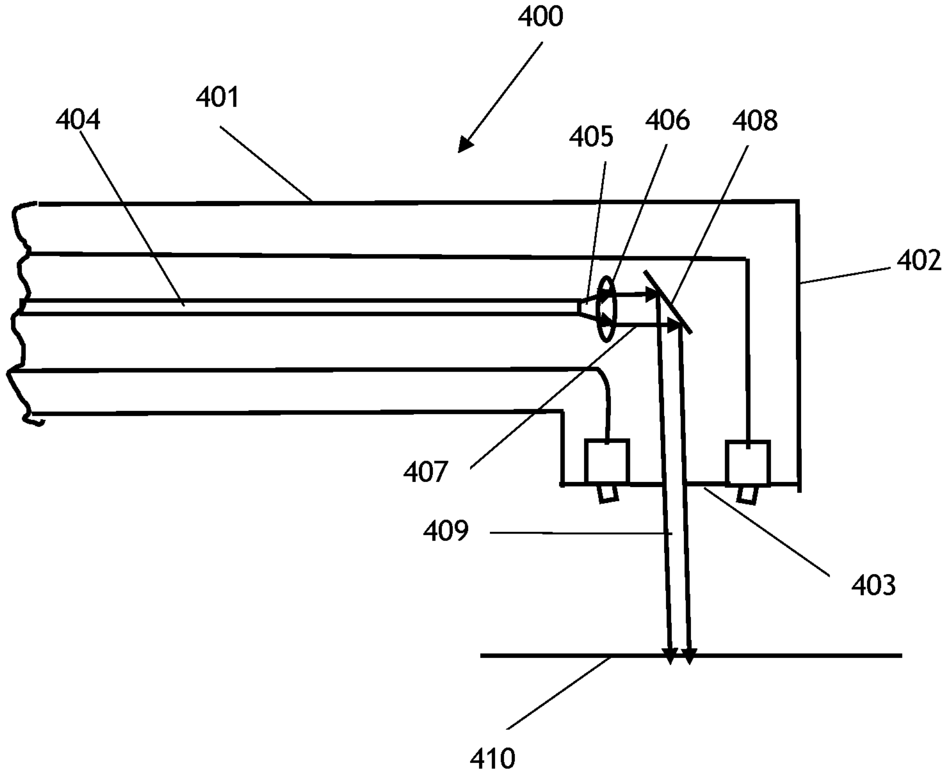
FIG. 4 is another schematic depicting an alternate head design, with reservoirs for liquids stored therein.

Other systems may adapt how the laser is delivered, such as the embodiment shown in FIG. 4. In this embodiment (400), the deliveries of dye and rinse solutions are the same as described in FIG. 3, where (401) is the casing of handpiece with distal end (402) and exit (403) for laser beam, dye, and rinse solutions. However, inside the handpiece there is a fiber (404) to deliver the laser beam (405) and at end of fiber (404) is a lens (406) to shape the beam. Beam may be focused or shaped into a parallel, collimated, beam (407). A reflector (408) is used to reflect the beam (407) by a 90° angle, thereby directing beam (409) to treatment surface (410).

Figure 5:
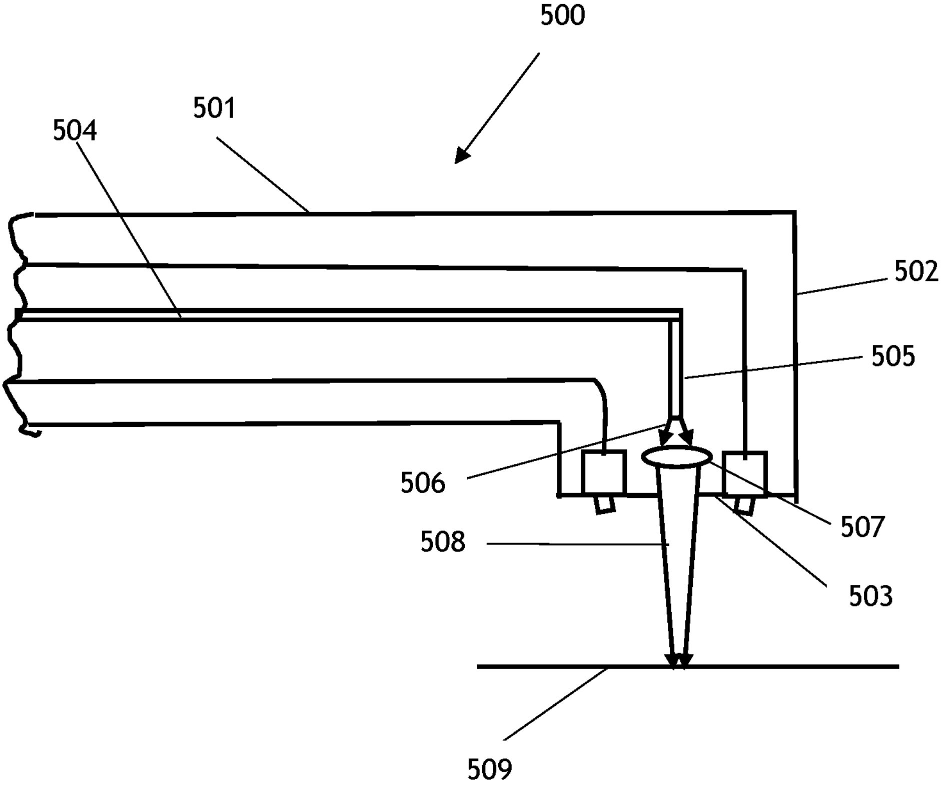
FIG. 5 is another schematic depicting an alternate head design, with reservoirs for liquids stored therein.

Further variation on the laser direction is shown in FIG. 5. In this embodiment (500) the deliveries of dye and rinse solutions are the same as described in FIG. 3, but the laser (506) is delivered through a fiber (504) that is bent 900 (505) and is then directed to lens (507) which adjusts the beam (508). Beam (508) may be a focused or parallel beam when is strikes the treatment surface (509).

INDUSTRIAL APPLICABILITY

The present invention may be manufactured in industry and has relevance in the medical and dental arts. the present invention has been described with reference to preferred embodiments, numerous modifications and variations can be made and still the result will come within the scope of the invention. No limitation with respect to the specific embodiments disclosed herein is intended or should be inferred.

What is claimed is:

1. A laser system comprising a laser control module, a control switch, and a handpiece, the handpiece further comprising:

a casing having a distal end and a proximal end;

a connection structure extending between the proximal end of the casing of handpiece to the laser control module, said connection structure containing a laser waveguide extending within the handpiece;

an exit for laser output contained within the distal end of the casing of the handpiece;

a dye nozzle contained within the distal end of the casing of the handpiece, proximate the exit for laser output;

a rinse nozzle contained within the distal end of the casing of the handpiece, proximate the exit for laser output and dye nozzle;

wherein the same handpiece may be utilized to sequentially apply a dye to a treatment surface, apply a laser to the dyed treatment surface, and apply a rinse agent to the treatment surface after the laser is used through a single actuation of the control switch.

2. The laser system of claim 1, the dye nozzle and rinse nozzle being supplied from a dye reservoir and a rinse reservoir, respectively, located within the laser control module, with supply tubing extending from said reservoirs to the dye nozzle and rinse nozzle.

3. The system of claim 1, the dye nozzle and rinse nozzle being supplied from a dye reservoir and a rinse reservoir, respectively, located within the handpiece.

4. A method of cutting tissues, the method comprising actuation of a single control switch which initiates the following sub-steps in succession:

a sub-step of supplying a laser system with a handpiece having an exit for a dye, a laser, and a rinse agent;

a sub-step of using the handpiece to apply a dye to a targeted area;

a sub-step of using the handpiece to apply a laser to the targeted area after said targeted area is dyed; and, a sub-step of using the handpiece to apply a rinse agent to the targeted area after the laser is applied thereto;

repeating the sub-steps until the control switch is deactivated.

* * * * *